(12) United States Patent
Han et al.

(10) Patent No.: US 8,829,218 B2
(45) Date of Patent: Sep. 9, 2014

(54) HIGHLY ACTIVE AND SELECTIVE ETHYLENE OLIGOMERIZATION CATALYST AND METHOD OF PREPARING HEXENE OR OCTENE USING THE SAME

(75) Inventors: Tack-Kyu Han, Daejeon (KR); Sang-Ook Kang, Yongin-si (KR); Sung-Kwan Kim, Gyeongsangnam-do (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 257 days.

(21) Appl. No.: 13/388,185

(22) PCT Filed: Mar. 3, 2010

(86) PCT No.: PCT/KR2010/001341
§ 371 (c)(1),
(2), (4) Date: Jan. 31, 2012

(87) PCT Pub. No.: WO2011/108772
PCT Pub. Date: Sep. 9, 2011

(65) Prior Publication Data
US 2012/0130086 A1     May 24, 2012

(51) Int. Cl.
*C07F 11/00* (2006.01)
*C07C 2/36* (2006.01)
*C08F 110/02* (2006.01)

(52) U.S. Cl.
CPC ............... *C07F 11/005* (2013.01); *C07C 2/36* (2013.01); *C08F 110/02* (2013.01); *C07C 2531/24* (2013.01)
USPC .......................................................... 556/18

(58) Field of Classification Search
CPC .................................................... C07F 11/005

USPC ............................................................ 556/18
See application file for complete search history.

(56) References Cited

U.S. PATENT DOCUMENTS 4,628,138 A    12/1986   Barnett et al.

FOREIGN PATENT DOCUMENTS

| KR | 1020060002741 A | 1/2006 |
| KR | 1020080068226 A | 7/2008 |
| KR | 1020080068227 A | 7/2008 |
| KR | 1020100087913 A | 8/2010 |
| WO | 0204119 A1 | 1/2002 |
| WO | 2004056477 A1 | 7/2004 |
| WO | 2004056479 A1 | 7/2004 |
| WO | 2008088178 A1 | 7/2008 |
| WO | 2009022770 A1 | 2/2009 |

OTHER PUBLICATIONS

Anthea Carter et al., "High activity ethylene trimerisation catalysts based on diphosphine ligands," Chem Commun., 2002, pp. 858-859.
Zhaofu Fei et al., "Influence of the functional group on the synthesis of aminophosphines, diphosphinoamines and iminobiphosphines," Dalton Trans., 2003, pp. 2772-2779.
Annette Bollmann et al., "Ethylene Tetramerization: A New Route to Produce 1-Octene in Exceptionally High Selectivities," J. Am. Chem. Soc., 2004, pp. 14712-14713, vol. 126, No. 45.
M. D. Fryzuk et al., "Asymmetric Synthesis, Production of Optically Active Amino Acids by Catalytic Hydrogenation," Journal of the American Chemical Society, Sep. 14, 1977, pp. 6262-6267, 99:19.
E. J. Corey et al., "L(+)-2,3-Butanedithiol: Synthesis and Application to the Resolution of Racemic Carbonyl Compounds," J. Am. Chem. Soc. Aug. 5, 1962, pp. 2938-2941, vol. 84.

*Primary Examiner* — Joseph Kosack
(74) *Attorney, Agent, or Firm* — The Webb Law Firm (57) ABSTRACT

This invention relates to a chromium complex compound for selective ethylene oligomerization including a chiral ligand, and to a method of selectively preparing 1-hexene or 1-octene from ethylene using the same.

17 Claims, 2 Drawing Sheets

HIGHLY ACTIVE AND SELECTIVE ETHYLENE OLIGOMERIZATION CATALYST AND METHOD OF PREPARING HEXENE OR OCTENE USING THE SAME

TECHNICAL FIELD

The present invention relates to a highly active and selective ethylene oligomerization catalyst for use in ethylene oligomerization such as trimerization or tetramerization and a method of preparing 1-hexene or 1-octene using the same, and more particularly to a chromium complex compound for selective ethylene oligomerization comprising a chromium compound and a chiral ligand having a specific stereoisomeric structure, to a chromium complex catalyst composition for selective ethylene oligomerization comprising the chromium complex compound for selective ethylene oligomerization and a co-catalyst such as methylaluminoxane (MAO), and to a method of preparing 1-hexene or 1-octene at high activity and high selectivity using such a catalyst system.

BACKGROUND ART 1-hexene and 1-octene, which are monomers or comonomers for producing linear low-density polyethylene, are an important industrial material widely used in a polymerization process, and are obtained by purifying products resulting from oligomerizing ethylene. However, conventional ethylene oligomerization is inefficient in terms of producing considerable amounts of butene, higher oligomers, and polyethylene, as well as 1-hexene and 1-octene. Such conventional ethylene oligomerization techniques typically produce a variety of α-olefins depending on the Schulze-Flory or Poisson product distribution, undesirably obtaining desired products in limited yield.

Recent research into the production of 1-hexene or 1-octene by selectivity trimerizing or tetramerizing ethylene using transition metal catalysis is ongoing, in which almost the known transition metal catalysts are chromium-based catalysts. International Patent Publication WO 02/04119 discloses an ethylene trimerization catalyst, namely, a chromium-based catalyst using a ligand of $(R^1)(R^2)X—Y—X(R^3)(R^4)$, in which X is phosphorus, arsenic or antimony, Y is a linker such as $—N(R^5)—$, and at least one of $R^1$, $R^2$, $R^3$ and $R^4$ has a polar substituent or an electron donating substituent.

Another publication discloses the use of a $(o\text{-ethylphenyl})_2$PN(Me)P$(o\text{-ethylphenyl})_2$ compound in which at least one of $R^1$, $R^2$, $R^3$ and $R^4$ has no polar substituent, as a ligand which does not exhibit catalytic activity for 1-hexene under catalytic conditions (Antea Carter et al., Chem. Commun., 2002, p. 858-859).

In addition, Korean Unexamined Patent Publication No. 2006-0002741 discloses that superior activity and selectivity of ethylene trimerization are actually possible using a PNP ligand containing a non-polar substituent at an ortho-position of a phenyl ring attached to phosphorus, such as $(o\text{-ethylphenyl})_2$PN(Me)P$(o\text{-ethylphenyl})_2$.

Also, International Patent Publication WO 04/056479 discloses increasing selectivity in the production of 1-octene by tetramerizing ethylene using a chromium-based catalyst containing a PNP ligand having no substitutent on a phenyl ring attached to phosphorus. As such, a heteroatomic ligand used for an ethylene tetramerization catalyst is exemplified by $(phenyl)_2$PN(isopropyl)P$(phenyl)_2$ or the like This conventional publication discloses that the chromium-based catalyst containing a heteroatomic ligand having nitrogen and phosphorus heteroatoms enables ethylene to be tetramerized even in the absence of a polar substituent on the hydrocarbyl or heterohydrocarbyl group bonded to the phosphorus atom, thus producing 1-octene at a selectivity exceeding 70 mass %.

However, the conventional techniques do not propose definite examples of the heteroatom-containing ligand structure which is capable of highly selectively tetramerizing or trimerizing ethylene to produce 1-octene or 1-hexene. As well, these techniques propose only a PNP-type backbone structure, such as $(R_1)(R_2)P—(R_5)N—P(R_3)(R_4)$ as a ligand having 1-octene selectivity of about 70 mass %. Furthermore, the forms of substituents that are substitutable in the heteroatomic ligands are limitedly provided. Specifically, although the tetramerization selectivity greatly depends on a bridge structure between a P atom and another P atom in the ligand backbone structure, the conventional techniques disclose that the catalyst is defined as a highly selective catalyst so long as P atoms are respectively connected to both sides of the bridge structure.

Also, the conventional PNP type backbone ligands having heteroatoms are problematic because in the preparation of 1-octene or 1-hexene the reaction activity is not uniformly maintained over time and the reaction rate is remarkably decreased. This is considered to be because the N atom of the ligand backbone structure may be easily coordinated with the transition metal due to the presence of an unshared electron pair thereof and thus may be adapted for a ligand but may be induced to easily dissociate from the transition metal by means of the P atom having comparatively poor coordination performance. The publication discloses facilitating the PNP backbone ligand to be converted from P—N—P into N=P—P depending on the synthesis conditions including the solvent and substituent polarity (Dalton Trans., 2003, 2772).

Also, another publication discloses that in the case of a heteroatom-containing PNP type backbone ligand, when ethylene oligomerization is performed using a catalyst complex already synthesized from the ligand and a chromium precursor, the reaction activity and selectivity are not greatly changed compared to when the ligand and the chromium precursor are separately added (J. Am. Chem. Soc., 2004, 126, 14712).

However, the aforementioned publications disclose only the very limited catalyst to actually prepare 1-hexene and 1-octene at high activity and high selectivity, in which the activity thereof is low, resulting in confined industrial applicability. In particular, the known catalysts are problematic because the expensive co-catalyst exemplified by methylaluminoxane is used, making it more difficult to achieve industrialization.

DISCLOSURE

Technical Problem

The present applicant has performed the ethylene oligomerization under conditions of variously changing not only the structure between P and P atoms but also substituents $R^1$, $R^2$, $R^3$, $R^4$ of the P atoms, in order to overcome conventional catalyst stability problems disclosed in Korean Patent Application No. 2007-0005688, and thus revealed the fact that a chromium-based catalyst system including a P—C—C—P backbone ligand without nitrogen may be used to trimerize or tetramerize ethylene to thus produce 1-hexene or 1-octene at high selectivity, and also that the activity of the catalyst may be considerably stabilized over reaction time so that the reaction rate is continuously maintained. Furthermore, the applicant has found that when structures adjacent to the C atoms between two P atoms in the P—C—C—P backbone ligand according to the present invention are sterically changed, the activity and selectivity of trimerization and tetramerization may be greatly enhanced.

However, in conventional techniques, when the transition metal and the P—C—C—P backbone ligand are separately added to an ethylene oligomerization medium, limitations are imposed on enhancing the activity and selectivity. The reason is that the carbon atom of the backbone structure has no unshared electron pair and the coordination direction of the transition metal is limited due to the chiral carbon of the backbone structure around the P atom functioning to donate electrons to the transition metal, thus making it difficult to approach the transition metal in the reaction medium to form a coordinate bond. The P—C—C—P backbone structure has steric and electronic effects in which when the transition metal precursor and the P—C—C—P backbone ligand are separately added to the ethylene oligomerization medium as a catalyst like the PNP ligand, the number of molecules of the transition metal precursor to be converted into catalytic active sites is reduced unlike the PNP ligand, resulting in lowered activity and selectivity upon trimerization or tetramerization of ethylene.

In order to overcome the limitation of enhancing the activity of the catalyst, the present applicant has synthesized a substantially pure transition metal complex by reacting a chiral ligand having a P—C—C—P backbone structure with a transition metal precursor and then introduced the synthesized transition metal complex to an ethylene oligomerization medium, and thus confirmed that the activity and selectivity of the catalyst are drastically increased, thereby completing the present invention.

Technical Solution

Therefore, the present invention is intended to provide a highly active and selective ethylene oligomerization catalyst for use in ethylene oligomerization such as trimerization or tetramerization, namely, a chromium complex compound for carrying out selective ethylene oligomerization comprising a chiral ligand having a P—C—C—P backbone structure and chromium bonded with each other, and to provide a chromium complex catalyst composition for selective ethylene oligomerization, comprising the chromium complex compound for selective ethylene oligomerization and a co-catalyst such as methylaluminoxane (MAO), and also to provide a method of preparing 1-hexene or 1-octene at high activity and high selectivity using such a catalyst system.

Hereinafter, a detailed description will be given of the present invention.

The present invention provides, as an ethylene oligomerization catalyst, a transition metal complex compound synthesized by coordinating a chiral ligand having a P—C—C—P backbone structure to a transition metal or a transition metal precursor. More specifically, the present invention provides a chromium complex compound for selective ethylene oligomerization including a chiral ligand, as represented by Formula 1 or 2 below.

[Formula 1]

[Formula 2]

[In Formula 1 or 2, $R^1$, $R^2$, $R^3$, $R^4$, $R^7$, $R^8$, $R^9$ and $R^{10}$ are each independently hydrocarbyl, substituted hydrocarbyl, heterohydrocarbyl, or substituted heterohydrocarbyl; $R^5$, $R^6$, $R^{11}$ and $R^{12}$ are each independently hydrocarbyl or substituted hydrocarbyl, or $R^5$ and $R^6$ or $R^{11}$ and $R^{12}$ may be bonded with hydrocarbylene, substituted hydrocarbylene, heterohydrocarbylene or substituted heterohydrocarbylene; $X^1$ to $X^6$ are each independently halogen, —$OR^{21}$, —$OCOR^{22}$ or —$NR^{23}R^{24}$, in which $R^{21}$, $R^{22}$, $R^{23}$ or $R^{24}$ is hydrogen, hydrocarbyl or heterohydrocarbyl; L is hydrocarbon or heterohydrocarbon; and * and ** are a chiral carbon position and are each independently (S) or (R) configuration.]

As such, hydrocarbyl or heterohydrocarbyl indicates a radical having one bonding position derived from hydrocarbon or heterohydrocarbon, and hydrocarbylene indicates a radical having two bonding positions derived from, hydrocarbon, in which the hetero means that carbon is substituted by O, S, or N atom.

In the chiral ligand according to the present invention, the chiral carbons at the * and ** positions have (R,R), (R,S), (S,R), (S,S) configuration pairs.

According to the present invention, the chromium complex compound for selective ethylene oligomerization of Formula 1 or Formula 2 includes a chiral ligand represented by Formulas 3 to 8 below.

[Formula 3]

(R),(R)-Chiraphos-mono Chromium complex

[Formula 4]

(S),(S)-Chiraphos-mono Chromium complex

[Formula 5]

meso-Chiraphos-mono Chromium complex

[Formula 6]

(R),(R)-Chiraphos-bis Chromium complex

[Formula 7]

(S),(S)-Chiraphos-bis Chromium complex

[Formula 8]

meso-Chiraphos-bi Chromium complex

As such, the substituents of Formulas 2 to 6 are defined as in Formulas 1 and 2.

The chromium complex compound for selective ethylene oligomerization of Formula 1 or 2 includes compounds of Formulas 9 to 14 below when $R^5$ and $R^6$ or $R^{11}$ and $R^{12}$ are bonded with hydrocarbylene, substituted hydrocarbylene, heterohydrocarbylene or substituted heterohydrocarbylene.

[Formula 9]

1,2-(R),(R)-trans-Cyclophos-mono Chromium complex

[Formula 10]

1,2-(S),(S)-trans-Cyclophos-mono Chromium complex

[Formula 11]

1,2-(R),(S)-cis-Cyclophos-mono Chromium complex

[Formula 12]

1,2-(R),(R)-trans-Cyclophos-bi Chromium complex

[Formula 13]

1,2-(S),(S)-trans-Cyclophos-bi Chromium complex

[Formula 14]

1,2-meso-cis-Cyclophos-bi Chromium complex

In Formulas 9 to 14, A is selected from among (C1-C5)alkylene and (C1-C5)alkenylene, in which the alkylene and alkenylene include, in the case of (C3-C5)alkylene and (C3-C5)alkenylene, those forming a fused ring with a structure to which (C5-C7)cycloalkyl or (C6-C10)aryl is adjacent.

The substituents $R^1$, $R^2$, $R^3$, $R^4$, $R^7$, $R^8$, $R^9$ and $R^{10}$ of the chiral ligand of the chromium complex compound for selective ethylene oligomerization represented by Formulas 1 to 14 are each independently (C6-C20)aryl, (C6-C20)ar(C1-C10)alkyl, (C1-C10)alkyl, (C2-C10)alkenyl, (C2-C10)alkynyl, (C3-C7)cycloalkyl, hetero(C5-C20)aryl, hetero(C3-C7)cycloalkyl or —$NR^{23}R^{24}$ in which $R^{23}$ or $R^{24}$ is (C1-C10)alkyl, or (C6-C20)aryl, and the substituents $R^2$, $R^3$, $R^4$, $R^7$, $R^8$, $R^9$ and $R^{10}$ may be further substituted by one or more selected from among (C1-C10)alkyl, (C1-C10)alkoxy, (C6-C20)aryloxy and halogen.

Specifically, $R^1$, $R^2$, $R^3$, $R^4$, $R^7$, $R^8$, $R^9$ and $R^{10}$ of the chiral ligand are each independently selected from the group consisting of phenyl, naphthyl, mesityl, methyl, ethyl, ethylenyl, n-propyl, i-propyl, propenyl, propynyl, n-butyl, t-butyl, cyclopropyl, cyclobutyl, cyclopentyl, cyclohexyl, 4-methylcyclohexyl, 4-ethylcyclohexyl, 4-isopropylcyclohexyl, benzyl, tolyl, xylyl, 4-methylphenyl, 4-ethylphenyl, 4-isopropylphenyl, 4-t-butylphenyl, 4-methoxyphenyl, 4-isopropoxyphenyl, cumyl, methoxy, ethoxy, phenoxy, tolyloxy, dimethylamino, thiomethyl, trimethylsilyl, dimethylhydrazyl, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl, o-isopropoxyphenyl, biphenyl, naphthyl and anthracenyl, and preferably are each independently selected from the group consisting of phenyl, benzyl, naphthyl, 4-methylphenyl, 4-ethylphenyl, 4-isopropylphenyl, 4-t-butylphenyl, 4-methoxyphenyl, 4-isopropoxyphenyl, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl and o-isopropoxyphenyl.

In the present invention, $R^5$, $R^6$, $R^{11}$ and $R^{12}$ which are bonded with a chiral carbon of the chiral ligand contained in the chromium complex compound for selective ethylene oligomerization are each independently (C6-C20)aryl, (C6-C20)ar(C1-C10)alkyl, (C1-C10)alkyl, (C2-C10)alkenyl, (C2-C10)alkynyl, (C3-C7)cycloalkyl, hetero(C5-C20)aryl, hetero(C3-C7)cycloalkyl, (C1-C10)alkoxy, (C6-C20)aryloxy, aminocarbonyl, carbonylamino, di(C1-C10)alkylamino, (C1-C10)alkylsilyl or (C6-C20)arylsilyl, and the substituents $R^5$, $R^6$, $R^{11}$ and $R^{12}$ may be substituted by (C1-C10)alkyl, (C1-C10)alkoxy, (C6-C20)aryloxy and halogen, and are preferably selected from among methyl, ethyl, ethylenyl, n-propyl, i-propyl, propenyl, propynyl, n-butyl, t-butyl, i-butyl, phenyl, benzyl, tolyl, xylyl, methoxy, ethoxy, phenoxy, methylamino, and dimethylamino.

In the chromium complex compound for selective ethylene oligomerization, $X^1$, $X^2$, $X^3$, $X^4$, $X^5$ or $X^6$ which is coordinated to chromium may be selected from among Cl, Br, acetoacetyl and 2-ethylhexanoyl, but the present invention is not limited thereto.

In Formula 1, L which is coordinated to chromium may be selected from among tetrahydrofuran, diethylether, toluene, chlorobenzene, dichlorobenzene, acetylacetone and 2-ethylhexanone, and L is derived from solvents which can be a medium for the reaction between the chiral ligand and the chromium salt.

Examples of the chiral ligand of the chromium complex compound for selective ethylene oligomerization according to the present invention include the following compounds, which do not confine the present invention.

(S,S)-, (R,R)- or meso-(phenyl)$_2$P—CH(methyl)CH(methyl)-P(phenyl)$_2$,
(S,S)-, (R,R)- or meso-(4-methoxyphenyl)$_2$P—CH(methyl)CH(methyl)-P(4-methoxyphenyl)$_2$,
(S,S)-, (R,R)- or meso-(4-methylphenyl)$_2$P—CH(methyl)CH(methyl)-P(4-methylphenyl)$_2$,
(R,R)- or meso-(4-ethylphenyl)$_2$P—CH(methyl)CH(methyl)-P(phenyl)$_2$,
(R,R)- or meso-(4-ethylphenyl)$_2$P—CH(ethyl)CH(methyl)-P(4-ethylphenyl)$_2$,
(S,S)-, (R,R)- or meso-(4-methoxyphenyl)$_2$P—CH(ethyl)CH(methyl)-P(phenyl)$_2$
(S,S)-, (R,R)- or meso-(4-ethylphenyl)$_2$P—CH (ethyl)CH(ethyl)-P(4-ethylphenyl)$_2$,
(S,S)-, (R,R)- or meso-(phenyl))$_2$P—CH(ethyl)CH(ethyl)-P(phenyl))$_2$,
(S,S)-, (R,R)- or meso-(phenyl))$_2$P—CH(isopropyl)CH(methyl)-P(Phenyl)$_2$,
(S,S)-, (R,R)- or meso-(4-methoxyphenyl)$_2$P—CH(isopropyl)CH(methyl)-P(4-methoxyphenyl)$_2$,
(S,S)-, (R,R)- or meso-(4-ethylphenyl)$_2$P—CH(isopropyl)CH(methyl)-P(4-ethylphenyl)$_2$,
(S,S)-, (R,R)- or meso-(phenyl))$_2$P—CH(n-propyl)CH(methyl)-P(phenyl)$_2$,
(S,S)-, (R,R)- or meso-(4-methoxyphenyl)$_2$P—CH(n-propyl)CH(methyl)-P(4-methoxyphenyl)$_2$,
(S,S)-, (R,R)- or meso-4 (4-ethylphenyl)$_2$P—CH(n-propyl)CH(methyl)-P(4-ethylphenyl)$_2$,
(S,S)-, (R,R)- or meso-(phenyl))$_2$P—CH(isopropyl)CH(ethyl)-P(phenyl)$_2$,
(S,S)-, (R,R)- or meso-(4-methoxyphenyl)$_2$P—CH(isopropyl)CH(ethyl)-P(4-methoxyphenyl)$_2$,
(S,S)-, (R,R)- or meso-(4-ethylphenyl)$_2$P—CH(isopropyl)CH(ethyl)-P(4-ethylphenyl)$_2$,
(S,S)-trans, (R,R)-trans- or meso-cis-1,2-di-(P(phenyl)$_2$)cyclohexane,
(S,S)-trans, (R,R)-trans- or meso-cis-1,2-di-(P(4-methoxyphenyl)$_2$)cyclohexane,
(S,S)-trans, (R,R)-trans- or meso-cis-1,2-di-(P(4-ethylphenyl)$_2$)cyclohexane,
(S,S)-trans, (R,R)-trans- or meso-cis-trans-1,2-di-(P(phenyl)$_2$)cyclopentane,
(S,S)-trans, (R,R)-trans- or meso-cis-1,2-di-(P(4-methoxyphenyl)$_2$)cyclopentane,
(S,S)-trans, (R,R)-trans- or meso-cis-1,2-di-(P(4-ethylphenyl)$_2$)cyclopentane,
(S,S)-trans, (R,R)-trans- or meso-cis-3,4-di-(P(phenyl)$_2$)pyrrole,
(S,S)-trans, (R,R)-trans- or meso-cis-3,4-di-(P(4-methoxyphenyl)$_2$)pyrrole,
(S,S)-trans, (R,R)-trans- or meso-cis-3,4-di-(P(4-ethylphenyl)$_2$)pyrrole,
(S,S)-trans, (R,R)-trans- or meso-cis-3,4-di-(P(4-ethylphenyl)$_2$)imidazole,
(S,S)-, (R,R)- or meso-(4-ethylphenyl)$_2$P—CH(dimethylamine)CH(dimethylamine)-P(4-ethylphenyl)$_2$,
(S,S)-, (R,R)- or meso-(3-methoxyphenyl)$_2$P—CH(methyl)CH(methyl)-P(3-methoxyphenyl)$_2$,
(S,S)-, (R,R)- or meso-(4-ethoxyphenyl)$_2$P—CH(methyl)CH(methyl)-P(o-ethoxyphenyl)$_2$,
(S,S)-, (R,R)- or meso-4-(dimethylaminephenyl)$_2$P—CH(methyl)CH(methyl)P(4-dimethylaminephenyl)$_2$,
(S,S)-, (R,R)- or meso-(4-ethylcyclohexyl)$_2$PCH(methyl)CH(methyl)P(4-ethylcyclohexyl)$_2$,
(S,S)-, (R,R)- or meso-(2-ethylphenyl)$_2$PCH(methyl)CH(methyl)P(2-ethylphenyl)$_2$,
(S,S)-, (R,R)- or meso-(2-isopropylphenyl)$_2$PCH(methyl)CH(methyl)P(2-isopropylphenyl)$_2$,
(S,S)-, (R,R)- or meso-(2-methylphenyl)$_2$PCH(methyl)CH(methyl)P(2-methylphenyl)$_2$,
(S,S)-, (R,R)- or meso-(2-ethylphenyl)$_2$PCH(methyl)CH(methyl)P(phenyl)$_2$,
(S,S)-, (R,R)- or meso-(2-ethylphenyl)$_2$PCH (ethyl)CH(methyl)P(2-ethylphenyl)$_2$,
(R,R)- or meso-(2-ethylphenyl)$_2$PCH(ethyl)CH(ethyl)P(2-ethylphenyl)$_2$,
(S,S)-, (R,R)- or meso-(2-ethylphenyl)$_2$PCH(isopropyl)CH(methyl)P(2-ethylphenyl)$_2$,
(S,S)-, (R,R)- or meso-(2-ethylphenyl)$_2$PCH (n-propyl)CH(methyl)P(2-ethylphenyl)$_2$,
(S,S)-, (R,R)- or meso-(2-ethylphenyl)$_2$PCH(isopropyl)CH(ethyl)P(2-ethylphenyl)$_2$,
(S,S)-trans, (R,R)-trans- or meso-cis-1,2-di-(P (2-ethylphenyl)$_2$)cyclohexane,
(S,S)-trans, (R,R)-trans- or meso-cis-1,2-di-(P(2-ethylphenyl)$_2$)cyclopentane, (S,S)-trans, (R,R)-trans- or meso-cis-3,4-di-(P (2-ethylphenyl)$_2$) pyrrole, (S,S)-trans, (R,R)-trans- or meso-cis-3,4-di-(P(2-ethylphenyl)$_2$)imidazole, (S,S)-, (R,R)- or meso-(2-ethylphenyl)$_2$PCH(dimethylamine)CH(dimethylamine)P(2-ethylphenyl)$_2$, (S,S)-, (R,R)- or meso-(2-methoxyphenyl)$_2$PCH(methyl)CH(methyl)P(2-methoxyphenyl)$_2$, (S,S)-, (R,R)- or meso-(2-ethoxyphenyl)$_2$PCH(methyl)CH(methyl)P(2-ethoxyphenyl)$_2$, (S,S)-, (R,R)- or meso-(2-dimethylaminephenyl)$_2$PCH(methyl)CH(methyl)P(2-dimethylaminephenyl)$_2$, and (S,S)-, (R,R)- or meso-(2-ethylcyclohexyl)$_2$PCH(methyl)CH(methyl)P(2-ethylcyclohexyl)$_2$.

The chiral ligands according to the present invention may be prepared using a variety of methods known to those skilled in the art.

The P—C=C—P type stereoisomeric backbone structure of the ligand according to the present invention is different from that of a known conventional $(R)_n$PN(R')P$(R)_m$ heteroligand, and the heteroatom in the backbone structure of the ligand is only phosphorus (P). Specifically, the ligand used in the catalyst system according to the present invention is provided in the form of a carbon-carbon backbone structure without a N atom between two P atoms, and thus the spatial structure is appropriately adjusted in the arrangement direction of the substituents attached to the C atoms, thereby exhibiting superior catalytic activity, achieving a high 1-hexene or 1-octene selectivity of 70 wt % or more, and maintaining the reaction activity stable.

Also, the transition metal complex coordinated with the chiral ligand having a P—C—C—P backbone structure may be modified so as to be attached to a polymer chain in order to make it insoluble at room temperature or higher. Furthermore, this complex may be fixedly bonded to a backbone such as silica, silica gel, polysiloxane or alumina.

In addition, in order to achieve more effective activity and higher selectivity, the present invention provides a chromium complex catalyst composition for selective ethylene oligomerization, comprising the above chromium complex catalyst for selective ethylene oligomerization and a known co-catalyst.

The co-catalyst used in the catalyst composition according to the present invention may be any compound which activates the transition metal complex coordinated with the chiral ligand having a P—C—C—P backbone structure. The activator may also be used in a mixture. The compound adapted for the activator includes an organoaluminum compound, an organoboron compound, or an organic salt.

Examples of the organoaluminum compound suitable for use as the activator in the catalyst system according to the present invention includes AlR$_3$ (R is independently (C1-C12)alkyl, oxygen-containing (C1-C12)alkyl or halogen) or LiAlH$_4$.

In the catalyst composition according to the present invention, the co-catalyst includes trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, methylaluminum sesquichloride and aluminoxane.

Typically in the art, aluminoxane is widely known to be an oligomeric compound which may be prepared by appropriately mixing water and an alkylaluminum compound, for example, trimethylaluminum. The produced aluminoxane oligomeric compound may be a linear compound, a cyclic compound, a cage compound, or combinations thereof.

Suitable examples of the organoboron compound include boroxin, NaBH$_4$, triethylborane, triphenylborane, triphenylborane ammonia complexes, tributylborate, triisopropylborate, tris(pentafluorophenyl)borane, trityl(tetrapentafluorophenyl)borate, dimethylphenylammonium (tetrapentafluorophenyl)borate, diethylphenylammonium (tetrapentafluorophenyl)borate, methyldiphenylammonium (tetrapentafluorophenyl)borate, or ethyldiphenylammonium (tetrapentafluorophenyl)borate. This organoboron compound may be used in a mixture with the above organoaluminum compound.

In the co-catalyst, aluminoxane may be selected from among alkylaluminoxane, for example, methylaluminoxane (MAO) and ethylaluminoxane (EAO), and modified alkylaluminoxane, for example, modified methylaluminoxane (MAO). The modified methylaluminoxane (prepared by Akzo Nobel) contains a hybrid alkyl group such as isobutyl or n-octyl group, in addition to a methyl group.

Particularly useful as the co-catalyst is methylaluminoxane (MAO) or ethylaluminoxane (EAO).

The chromium complex for selective ethylene oligomerization and aluminoxane are mixed such that a molar ratio of aluminum to chromium ranges from 1:1 to 10,000:1, preferably about 1:1 to 1,000:1.

In addition, the present invention provides a method of preparing an oligomer, in particular, 1-hexene or 1-octene at high activity and high selectivity, which includes preparing the chromium complex compound for selective ethylene oligomerization of Formula 1 or 2 including a transition metal precursor coordinated with a chiral ligand having a P—C—C—P backbone structure, and adding the chromium complex compound thus prepared to an ethylene oligomerization medium so that ethylene is oligomerized at high activity and high selectivity, in which the P—C—C—P backbone ligand adapted to achieve high activity and high selectivity may be (S,S)-, (R,R)- or meso-isomeric linear, trans- or cis-cyclic. Also useful as a mixture of some isomers may be a multi-ligand in which (S,S)-, (R,R)- or meso-(R$_1$) (R$_2$)P—(R$_5$)CHCH(R$_6$)—P(R$_3$)(R$_4$) ligands are bonded with each other.

The chromium complex for selective ethylene oligomerization and the co-catalyst, which are individual components of the catalyst system disclosed in the present invention, may be mixed simultaneously or sequentially in any order in the presence or absence of a solvent, thus preparing an active catalyst. These catalyst components may be mixed at a temperature ranging from −20 to 250° C. In the course of mixing the catalyst components, olefin may typically exhibit protective effects resulting in improved catalytic performance. Preferably, the mixing is performed at a temperature ranging from 20 to 100° C.

The reaction product disclosed in the present invention, that is, an ethylene oligomer, in particular, 1-hexene or 1-octene may be prepared using the chromium complex compound for selective ethylene oligomerization according to the present invention by means of a typical apparatus and a catalytic technique in the presence or absence of an inert solvent by a homogeneous liquid reaction, a slurry reaction in which the catalyst system is not partially or completely dissolved, a two-phase liquid/liquid reaction, a bulky reaction in which an olefin product acts as a main medium, or a gaseous reaction.

The method of selectively preparing an oligomer according to the present invention may be performed in the presence of an inert solvent. Specifically, any inert solvent which does not react with the catalyst compound and the activator may be used, and the inert solvent may include any saturated aliphatic and unsaturated aliphatic and aromatic hydrocarbons and hydrocarbon halides. Typical examples of the solvent include but are not limited to benzene, toluene, xylene, chlorobenzene, cumene, heptane, cyclohexane, methylcyclohexane, methylcyclopentane, n-hexane, 1-hexene, 1-octene, etc. In particular when the compound of Formula 1 is used, the same compound as the L ligand is preferably used as a reaction solvent.

In the preparation method according to the present invention, oligomerization may be carried out at a temperature ranging from −20 to 250° C., preferably from 15 to 130° C., and more preferably from 30 to 70° C.

Furthermore, the method according to the present invention is performed at a pressure from atmospheric pressure to 500 bar, preferably from 10 to 70 bar, and more preferably from 30 to 50 bar.

In an embodiment of the present invention, the P—C—C—P backbone stereoisomeric ligand coordination complex and the reaction conditions are selected so that the yield of 1-hexene from ethylene is 50 mass % or more, and preferably 70 mass % or more. In this case, the yield indicates the number of grams of 1-hexene formed per 100 g of the total reaction product.

In another embodiment of the present invention, the P—C—C—P backbone stereoisomeric ligand coordination complex and the reaction conditions are selected so that the yield of 1-octene from ethylene is 30 mass % or more, and preferably 50 mass % or more. In this case, the yield indicates the number of grams of 1-octene formed per 100 g of the total reaction product.

In the method according to the present invention, depending on the P—C—C—P backbone ligand and the reaction conditions, not only 1-hexene or 1-octane, but also different amounts of 1-butene, 1-hexene, methylcyclopentane, methylenecyclopentane, propylcyclopentane and a number of higher oligomers and polyethylenes may be provided.

The method according to the present invention may be performed using a plant including any type of reactor. Examples of the reactor may include but are not limited to a batch reactor, a semi-batch reactor, and a continuous reactor. The plant may include a combination of a reactor, an inlet for introducing olefin and the catalyst system into the reactor, a line for discharging an oligomerized reaction product from the reactor, and at least one separator for separating the oligomerized reaction product, in which the catalyst system may include the transition metal compound, the activator, and the P—C—C—P ligand coordination complex, as disclosed herein.

In the present invention, 1-hexene or 1-octene can be produced at high activity and high selectivity by oligomerizing ethylene using the ethylene oligomerization catalyst system according to the present invention.

Advantageous Effects

When a ligand and a chromium metal or chromium precursor are separately added to an oligomerization reaction medium, a considerable amount of the ligand cannot approach the chromium atom or cannot be normally coordinated, undesirably making it impossible to obtain activity and selectivity adapted for industrialization. However, according to the present invention, the case where ethylene is oligomerized using a chromium complex compound for selective ethylene oligomerization having a chiral P—C—C—P backbone structure is advantageous because the catalyst in which the chiral ligand is normally coordinated to chromium is used, the reaction activity is increased 10 times or more, and the selectivity is increased, so that the amount of polymer by-product is reduced to 1/10 or less, and consequently the amount of polymer by-product after reaction can be effectively lowered to about 0.1 wt %, thus simplifying the purifying process to thereby favorably perform the production process. Furthermore, the amount of an expensive co-catalyst such as MAO necessary for activating the catalyst can be reduced to 1/10 or less, resulting in economical production process.

MODE FOR INVENTION

A better understanding of the present invention may be obtained through the following examples which are set forth to illustrate, but are not to be construed as limiting the present invention.

Preparative Example

Catalyst Preparation Example 1

Preparation of (S,S)-(phenyl)$_2$PCH(methyl)CH(methyl)P(phenyl)$_2$ chromium trichloride tetrahydrofuran [CrCl$_3$(THF){(P,P)-k$^2$-(S,S)—((Ph)$_2$P(Me)CH—CH(Me)P(Ph)$_2$)}]

A. Preparation of Ligand (S,S)-(Phenyl)$_2$PCH(methyl)CH(methyl)P(phenyl)$_2$[(S,S)-Ph$_2$PCH(Me)CH(Me)PPh$_2$]

A chiral ligand [(S,S)-Ph$_2$PCH(Me)CH(Me)PPh$_2$] was prepared as disclosed in B. Bosnich et al, J. Am. Chem. Soc. 99(19) (1977) 6262. (2R,3R)-butanediol di-p-toluenesulfonate was prepared from (2R,3R)-butanediol. This method was performed as disclosed in R. B. Mitra et al, J. Am. Chem. Soc 84 (1962). 100 mL (1.24 mol) of dry pyridine was added to a 1 L flask cooled in an ice bath and then mixed with 100 g (0.525 mol) of p-toluenesulfonyl chloride, after which 22 mL (0.245 mol) of (2R,3R)-butanediol was slowly added dropwise thereto. The mixture was warmed to room temperature for 20 min, and then allowed to stand in a semi-solid phase at room temperature for 12 hours. Excess ice pieces were added to the mixture, and the flask was vigorously shaken so that the mixture did not conglomerate. Whether powdery crystals were slowly precipitating was checked, after which the mixture was stirred for 2 hours along with ice pieces, and then crushed ice pieces and 70 mL of a concentrated hydrochloric acid solution were added thereto with vigorous stirring. The extracted slurry was filtered, thoroughly washed with water, and dried, thus obtaining 85 g (86.3%) of a (2R,3R)-butanediol di-p-toluenesulfonate product (mp 62~64° C.).

On the other hand, 95 g of recrystallized triphenylphosphorus and 300 mL of dry tetrahydrofuran (THF) were added into a 1 L three-neck round-bottom flask equipped with a 250 mL addition funnel, a reflux condenser and a nitrogen inlet. To the solution, 5.0 g of thin lithium pieces were added at 25° C. in a nitrogen atmosphere with stirring, thus forming LiPPh$_2$ in the solution. As such, the solution turned to a deep reddish yellow color while a large amount of heat was generated. The temperature of the solution was elevated slowly to 55° C. for 1 hour, and the solution was cooled again to 25° C. for 2 hours with stirring. The formed phenyllithium was decomposed by dropwise adding 33 g of distilled and purified t-butylchloride for 45 min. The transparent reddish yellow solution was boiled for 5 min, and then cooled again to −4° C.

To the cooled solution, 35 g of the above-prepared (2R, 3R)-butanediol di-p-toluenesulfonate, dissolved in 100 mL of dry THF, was added dropwise for 1 hour. The solution was warmed slowly to room temperature, and then stirred for 30 min. 300 mL of nitrogen-purged water was then added thereto, and THF was removed by distillation under reduced pressure, thus extracting a colorless oil-type product. The product was extracted two times with 150 mL of ether, and then dried with $Na_2SO_4$. The ether extract was filtered with a solution of 15 g of nickel perchlorate hexahydrate in 50 mL of ethanol in a nitrogen atmosphere. $Na_2SO_4$ remaining in the filter was thoroughly washed with ether, and then the ether solution was added to the nickel solution. The reddish brown oil-type product, which had yellow crystals, was [Ni((S,S)-chiraphos)$_2$](ClO$_4$)$_2$. The oil crystal mixture was added to a solution of 15 g of sodium thiocyanate (NaNCS) in 50 ml of hot ethanol, and the solution was vigorously stirred for a few hours until a uniform yellowish brown solid [Ni((S,S)-chiraphos)$_2$NCS]NCS was formed. This solid product was completely washed with ethanol, and then washed with ether.

15 g of the nickel complex thus prepared was suspended in 150 mL of ethanol under nitrogen and heated with stirring. 4 g of sodium cyanide (NaCN) was rapidly added to 20 g of water. The nickel complex was slowly dissolved to produce a clear red solution, [Ni((S,S)-chiraphos)$_2$CN$_3$]$^-$, which was then changed to a turbid beige-colored solution. The hot solution was stirred until a yellow slurry was formed. The slurry solution was cooled, and the solid was continuously washed two times with 25 mL of water and then rapidly cooled with ice-cooled ethanol. The impurity-containing beige-colored solid was dried at 25° C., added to 125 mL of boiling anhydrous ethanol, and then filtered using a Fritz filter. The Fritz filtration was performed at room temperature for 12 hours, thus obtaining a colorless glossy solid. The solid was then recrystallized from 60 mL of anhydrous ethanol, thereby attaining 5.5 g of completely colorless pure (S,S)-(phenyl)$_2$PCH(methyl)CH(methyl)P(phenyl)$_2$.

B. Preparation of (S,S)-(phenyl)$_2$PCH(methyl)CH(methyl)P(phenyl)$_2$ chromium trichloride tetrahydrofuran [CrCl$_3$(THF){(P,P)-k$^2$-(S,S)—((Ph)$_2$P(Me)CH—CH(Me)P(Ph)$_2$)}]

1.1 g (3.0 mmol) of chromium trichloride tris-tetrahydrofuran (CrCl$_3$(THF)$_3$) was dissolved in 100 mL of tetrahydrofuran, to which a solution of 1.28 g (3.0 mmol) of the above-prepared (S,S)-(phenyl)$_2$PCH(methyl)CH(methyl)P(phenyl)$_2$ ligand compound in 50 mL of tetrahydrofuran was then slowly added, and the resulting reaction solution was stirred at room temperature. The reaction solution was further stirred for 1 hour and volatile compounds were removed therefrom in a vacuum, after which 100 mL of petroleum ether was added dropwise to the reaction product, thus obtaining a precipitated blue solid. Two washings with 100 mL of petroleum ether were performed, giving 1.77 g (yield 90%) of the product.

Catalyst Preparation Example 2

Figure 1:
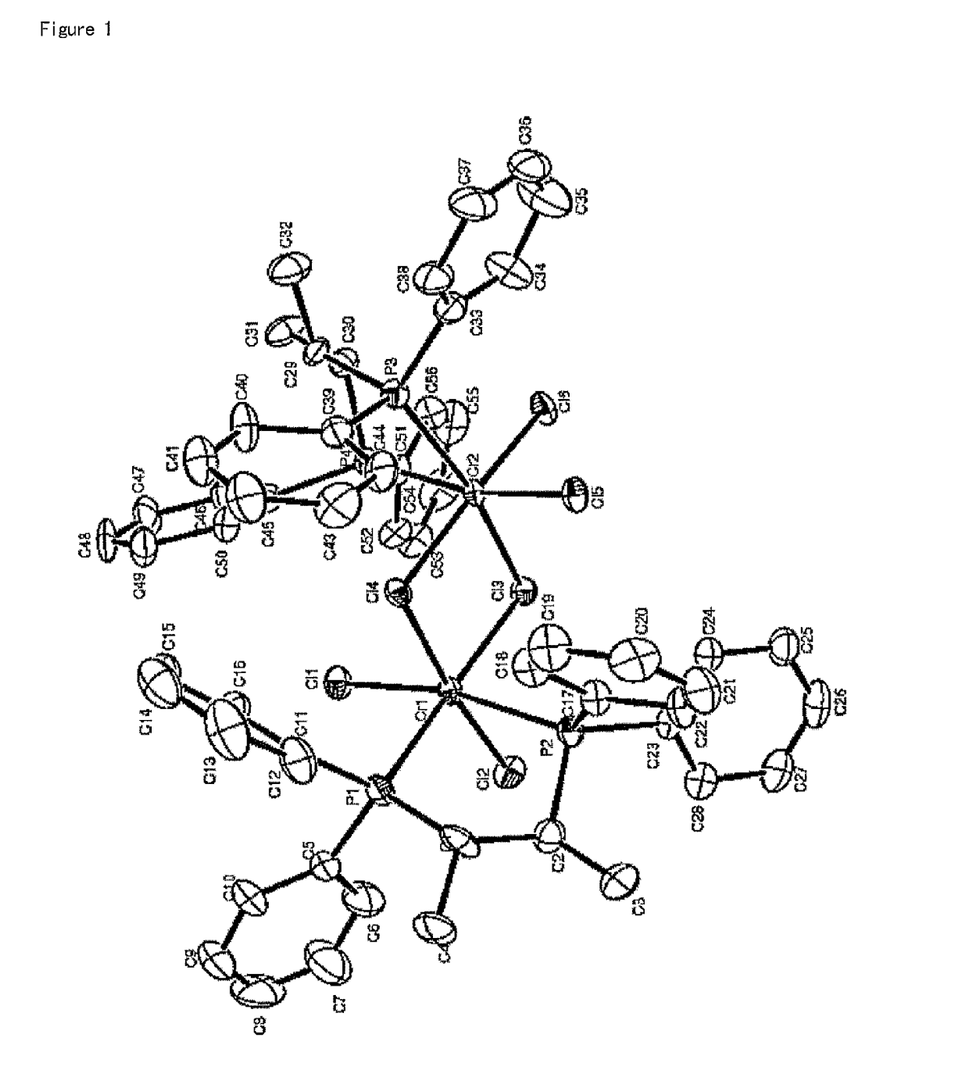
FIG. 1 shows the X-ray diffraction structure of the compound prepared in Catalyst Preparation Example 2.

Preparation of Bis-[(S,S)-(Phenyl)$_2$PCH(methyl)CH(methyl)P(phenyl)$_2$ chromium dichloride (μ-chloride)][CrCl$_2$(μ-Cl){(P,P)-k$^2$-(S,S)—((Ph)$_2$P(Me)CH—CH(Me)P(Ph)$_2$)}]$_2$ 1.1 g (3.0 mmol) of chromium trichloride tris-tetrahydrofuran (CrCl$_3$(THF)$_3$) was dissolved in 100 mL of dichloromethane, to which a solution of 1.28 g (3.0 mmol) of the (S,S)-(phenyl)$_2$PCH(methyl)CH(methyl)P(phenyl)$_2$ ligand compound prepared in Catalyst Preparation Example 1 in 50 mL of dichloromethane was then slowly added. The resulting reaction solution was further stirred for 1 hour and volatile compounds were then removed therefrom in a vacuum. 100 mL of petroleum ether was added dropwise to the product thus obtaining a blue solid precipitate, which was then washed two times with 100 mL of petroleum ether, giving 1.58 g (yield 90%) of the title compound. The complex compound thus prepared was analyzed using single-crystal X-ray diffraction. The structure thereof is shown in FIG. 1.

Catalyst Preparation Example 3

Preparation of [(S,S)-(phenyl)$_2$PCH(methyl)CH(methyl)P(phenyl)$_2$ chromium diacetylacetonate][Cr{(O,O)-k$^2$-(CH$_3$COCH$_2$COCH$_3$)$_2$}{(P,P)-k$^2$-(S,S)—((Ph)$_2$ P(Me)CH—CH(Me)P(Ph)$_2$)}]

1.62 g of the title compound was prepared in the same manner as in Catalyst Preparation Example 2, with the exception that 1.1 g (3.0 mmol) of chromium triacetylacetonate (Cr(acac)$_3$) was used in lieu of chromium trichloride tris-tetrahydrofuran (CrCl$_3$(THF)$_3$).

Catalyst Preparation Example 4

Preparation of [(S,S)-(phenyl)$_2$PCH(methyl)CH(methyl)P(phenyl)$_2$ chromium di(2-ethylhexanoate)][Cr{(OOCCH(C$_2$H$_5$)C$_4$H$_9$)$_2$}{(P,P)-k$^2$-(S,S)—((Ph)$_2$P(Me)CH—CH(Me)P(Ph)$_2$)}]

1.82 g of the title compound was prepared in the same manner as in Catalyst Preparation Example 2, with the exception that 1.44 g (3.0 mmol) of chromium tri(2-ethyl)hexanoate (Cr(OOCCH(C$_2$H$_5$)C$_4$H$_9$)$_3$) was used in lieu of chromium trichloride tris-tetrahydrofuran (CrCl$_3$(THF)$_3$).

Catalyst Preparation Example 5

Preparation of Bis-[(R,R)-(phenyl)$_2$PCH(methyl)CH(methyl)P(phenyl)$_2$ chromium dichloride (μ-chloride)][CrCl$_2$(μ-Cl){(P,P)-k$^2$-(R,R)—((Ph)$_2$P(Me)CH—CH(Me)P(Ph)$_2$)}]$_2$ A. Preparation of Ligand (R,R)-(phenyl)$_2$PCH(methyl)CH(methyl)P(phenyl)$_2$[(R,R)-Ph$_2$PCH(Me)CH(Me)PPh$_2$]

5.1 g of the title compound was prepared in the same manner as in Catalyst Preparation Example 1, with the exception that (2S,3S)-butanediol was used as a starting material, in lieu of (2R,3R)-butanediol.

Figure 2:
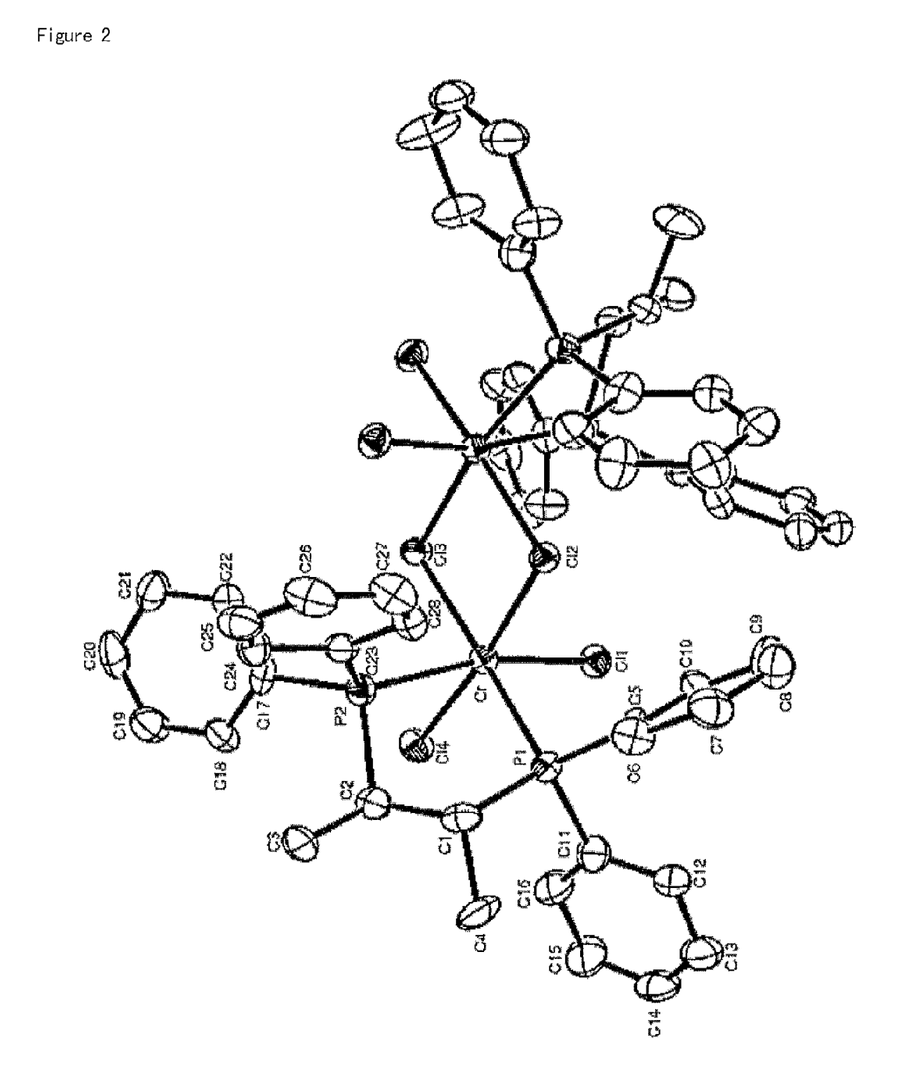
FIG. 2 shows the X-ray diffraction structure of the compound prepared in Catalyst Preparation Example 5.

B. Preparation of Bis-[(R,R)-(phenyl)$_2$PCH(methyl)CH(methyl)P(phenyl)$_2$ chromium dichloride (μ-chloride)][CrCl$_2$(μ-Cl){(P,P)-k$^2$-(R,R)—((Ph)$_2$P(Me)CH—CH(Me)P(Ph)$_2$)}]$_2$ 1.58 g of the title compound was prepared in the same manner as in Catalyst Preparation Example 2, with the exception that 1.28 g (3.0 mmol) of (R,R)-(phenyl)$_2$PCH(methyl)CH(methyl)P(phenyl)$_2$ ligand compound was used, in lieu of the (S,S)-ligand compound. The complex compound thus prepared was analyzed using single-crystal X-ray diffraction. The structure thereof is shown in FIG. 2.

Catalyst Preparation Example 6

Preparation of Bis-[meso-(phenyl)$_2$PCH(methyl)CH(methyl)P(phenyl)$_2$ chromium dichloride (μ-chloride)][CrCl$_2$(μ-Cl) {(P,P)-k$^2$-meso-((Ph)$_2$P(Me)CH—CH(Me)P(Ph)$_2$)}]$_2$ A. Preparation of Ligand meso-(phenyl)$_2$PCH(methyl))CH(methyl)P(phenyl)$_2$[meso-Ph$_2$PCH(Me)CH(Me)PPh$_2$]

5.7 g of completely colorless pure meso-(phenyl)$_2$PCH(methyl)CH(methyl)P(phenyl)$_2$ was prepared in the same manner as in Catalyst Preparation Example 1, with the exception that meso-butanediol was used as a starting material, in lieu of (2R,3R)-butanediol.

B. Preparation of Bis-[meso-(phenyl)$_2$PCH(methyl)CH(methyl)P(phenyl)$_2$ chromium dichloride (p-chloride)][CrCl$_2$(μ-Cl){(P,P)-k$^2$-meso-((Ph)$_2$P(Me)CH—CH(Me)P(Ph)$_2$)}]$_2$ 1.43 g of the title compound was prepared in the same manner as in Catalyst Preparation Example 2, with the exception that 1.28 g (3.0 mmol) of meso-(phenyl)$_2$PCH(methyl)CH(methyl)P(phenyl)$_2$ ligand compound was used, in lieu of the (S,S)-ligand compound.

Catalyst Preparation Example 7

Preparation of Bis-[(R,R)-(4-methoxyphenyl)$_2$PCH(methyl)CH(methyl)P(4-methoxyphenyl)$_2$ chromium dichloride (μ-chloride)][CrCl$_2$(μ-Cl){(P,P)-k$^2$-(R,R)-((4-MeOPh)$_2$P(Me)CH—CH(Me)P(4-MeOPh)$_2$)}]$_2$ A. Preparation of Ligand (R,R)-(4-methoxyphenyl)$_2$PCH(methyl)CH(methyl)P(4-methoxyphenyl)$_2$[(R,R)-(4-MeOPh)$_2$PCH(Me)CH(Me)P(4-MeOPh)$_2$]

The title compound was prepared as disclosed in B. Bosnich et al, J. Am. Chem. Soc 99(19) (1977).
The preparation of (2S,3S)-butanediol di-p-toluenesulfonate from (2S,3S)-butanediol was performed in the same manner as in Catalyst Preparation Example 1.
Tri(4-methoxyphenyl)phosphorus was prepared in the following manner. Magnesium pieces (91.1 g, 3.75 mol) were added dropwise to 95 mL (0.75 mol) of 4-bromo-anisol in 2 L of THF. After intensive reaction, the reaction mixture was heated under reflux for 2 hours to obtain a Grignard reagent. The Grignard reagent was added dropwise to a solution of 17.5 mL (0.2 mol) of PCl$_3$ in 2 L of THF at −78° C. over 2 hours with stirring. After completion of the dropwise addition, the dry ice/acetone bath was removed, and the reaction solution was warmed to room temperature. The reaction solution was stirred overnight, and the solvent was removed therefrom in a vacuum. The phosphine product was entirely used in a subsequent step without being removed.
Into a 1 L three-neck round-bottom flask equipped with a 250 mL addition funnel, a reflux condenser and a nitrogen inlet, 70 g of recrystallized tri(4-methoxyphenyl)phosphorus and 300 mL of dry THF were added. To the solution, 2.8 g of thin lithium pieces were added at 25° C. under nitrogen with stirring. LiP(4-OMe-Ph)$_2$ was immediately formed in the solution, and the solution turned to a deep reddish yellow color while a large amount of heat was generated. The temperature of the solution was elevated slowly to 55° C. for 1 hour, and the solution was cooled again to 25° C. for 2 hours with stirring. The formed 4-methoxyphenyllithium was decomposed by dropwise adding 18.5 g of distilled and purified t-butylchloride for 45 min. The transparent reddish yellow solution was boiled for 5 min, and then cooled again to −4° C.

To the cooled solution, 19.6 g of the above-prepared (2S,3S)-butanediol di-p-toluenesulfonate, dissolved in 100 mL of dry THF, was added dropwise for 1 hour. The solution was slowly warmed to room temperature, and then stirred for 30 min. 300 mL of nitrogen-purged water was added thereto, after which THF was removed by distillation under reduced pressure, thus extracting a colorless oil-type product. The product was extracted two times with 150 mL of ether, and then dried with Na$_2$SO$_4$. The ether extract was filtered with a solution of 8.4 g of nickel perchlorate hexahydrate in 50 mL of ethanol in a nitrogen atmosphere. Na$_2$SO$_4$ remaining in the filter was thoroughly washed with ether, and then the ether solution was added to the nickel solution. The reddish brown oil-type product was [Ni((2R,3R)-bis(di-p-methoxyphenyl)phosphorus butane)$_2$](ClO$_4$)$_2$. The oil crystal mixture was added to 8.4 g of sodium thiocyanate (NaNCS) dissolved in 50 mL of hot ethanol, and the solution was intensively stirred for a few hours until a uniform yellowish brown solid [Ni((2R,3R)-bis(di-p-methoxyphenyl)phosphorus butane)$_2$NCS]NCS was formed. The solid product was completely washed with ethanol, and then washed with ether.

17 g of the nickel complex was suspended in 150 mL of ethanol under nitrogen and heated with stirring. A solution of 4 g of sodium cyanide (NaCN) in 20 g of water was rapidly added thereto. The nickel complex was slowly dissolved to produce a clear red solution [Ni((2R,3R)-bis(di-p-methoxyphenyl)phosphorus butane)$_2$CN$_3$]$^-$, which was then changed to a turbid beige-colored solution. The hot solution was stirred until a yellow slurry was formed. The slurry solution was cooled, and the solid was continuously washed two times with 25 mL of water and rapidly cooled with ice-cooled ethanol. The impurity-containing beige-colored solid was dried at 25° C., added to 125 mL of boiling anhydrous ethanol, and then filtered using a Fritz filter. The Fritz filtration was performed at room temperature for 12 hours, whereby the filtrate was completely eliminated and only a colorless glossy solid remained. The solid was recrystallized from 60 mL of anhydrous ethanol, giving 6.2 g of completely colorless pure (R,R)-(4-methoxyphenyl)$_2$PCH(methyl)CH(methyl)P(4-methoxyphenyl)$_2$.

B. Preparation of Bis-[(R,R)-(4-methoxyphenyl)$_2$PCH(methyl)CH(methyl)P(4-methoxyphenyl)$_2$ chromium dichloride (μ-chloride)][CrCl$_2$(μ-Cl){(P,P)-k$^2$-(R,R)-((4-MeOPh)$_2$P(Me)CH—CH(Me)P(4-MeOPh)$_2$)}]$_2$ 1.29 g of the title compound was prepared in the same manner as in Catalyst Preparation Example 2, with the exception that 1.64 g (3.0 mmol) of (R,R)-(4-methoxyphenyl)$_2$PCH(methyl)CH(methyl)P(4-methoxyphenyl)$_2$ was used in lieu of (S,S)-(4-methoxyphenyl)$_2$PCH(methyl)CH(methyl)P(4-methoxyphenyl)$_2$.

Catalyst Preparation Example 8

Preparation of Bis-[(S,S)-(4-methylphenyl)$_2$PCH(methyl)CH(methyl)P(4-methylphenyl)$_2$ chromium dichloride (p-chloride)][CrCl$_2$(μ-Cl){(P,P)-k$^2$-(S,S)-((4-MePh)$_2$P(Me)CH—CH(Me)P(4-MePh)$_2$)}]$_2$ A. Preparation of Ligand (S,S)-(4-methylphenyl)$_2$PCH(methyl)CH(methyl)P(4-methylphenyl)$_2$[(S,S)-(4-MePh)$_2$PCH(Me)CH(Me)P(4-MePh)$_2$]

3.9 g of completely colorless pure (S,S)-(4-methylphenyl)$_2$P—CH(methyl)CH(methyl)P(4-methylphenyl)$_2$ was synthesized in the same manner as in Catalyst Preparation Example 7, with the exception that 4-tolyl-bromide was used to prepare tri(4-methylphenyl)phosphorus.

B. Preparation of Bis-[(S,S)-(4-methylphenyl)$_2$PCH(methyl)CH(methyl)P(4-methylphenyl)$_2$ chromium dichloride (p-chloride)][CrCl$_2$(μ-Cl){(P,P)-k$^2$-(S,S)-((4-MePh)$_2$P(Me)CH—CH(Me)P(4-MePh)$_2$)}]$_2$ 1.31 g of the title compound was prepared in the same manner as in Catalyst Preparation Example 2, with the exception that 1.45 g (3.0 mmol) of (R,R)-(4-methylphenyl)$_2$PCH(methyl)CH(methyl)P(4-methylphenyl)$_2$ ligand compound was used in lieu of (S,S)-(phenyl)$_2$PCH(methyl)CH(methyl)P(phenyl)$_2$.

Catalyst Preparation Example 9

Preparation of Bis-[(S,S)-(phenyl)$_2$PCH(phenyl)CH(phenyl)P(phenyl)$_2$ chromium dichloride (μ-chloride)][CrCl$_2$(μ-Cl){(P,P)-k$^2$-(S,S)—(Ph$_2$P(Ph)CH—CH(Ph)PPh$_2$)}]$_2$ A. Preparation of Ligand (S,S)-(phenyl)$_2$P—CH(phenyl)CH(phenyl)-P(phenyl)$_2$[(S,S)—(Ph$_2$P(Ph)CH—CH(Ph)PPh$_2$]

3.3 g of a colorless title compound was prepared in the same manner as in Catalyst Preparation Example 1, with the exception that (1R,2R)-1,2-diphenylethanediol was used as a starting material.

B. Preparation of Bis-[(S,S)-(phenyl)$_2$PCH(phenyl)CH(phenyl)P(phenyl)$_2$ chromium dichloride (p-chloride)][CrCl$_2$ (μ-Cl){(P,P)-k$^2$-(S,S)—(Ph$_2$P(Ph)CH—CH(Ph)PPh$_2$)}]$_2$ 0.9 g of the title compound was prepared in the same manner as in Catalyst Preparation Example 2, with the exception that 1.35 g (3.0 mmol) of (S,S)-(phenyl)$_2$P—CH(phenyl)CH(phenyl)-P(phenyl)$_2$ ligand compound was used in lieu of (S,S)-(phenyl)$_2$PCH(methyl)CH(methyl)P(phenyl)$_2$.

Catalyst Preparation Example 10

Preparation of Bis-[{(1S,2S)-trans-bis(diphenylphosphino)cyclohexane}chromium dichloride (μ-chloride)][CrCl$_2$(μ-Cl){(P,P)-k$^2$-(1S,2S)-(Ph$_2$P)$_2$cyclohexane}]$_2$ A. Preparation of Ligand (1S,2S)-trans-bis(diphenylphosphino)cyclohexane [(1S,2S)—(Ph$_2$P)$_2$cyclohexane}]$_2$ 3.6 g of a completely colorless pure title compound was prepared in the same manner as in Catalyst Preparation Example 1, with the exception that (1R,2R)-trans-cyclohexanediol was used as a starting material in lieu of (2R,3R)-butanediol.

B. Preparation of Bis-[{(1S,2S)-trans-bis(diphenylphosphino)cyclohexane}chromium dichloride (μ-chloride)][CrCl$_2$(μ-Cl){(P,P)-k$^2$-(1S,2S)—(Ph$_2$P)$_2$cyclohexane}]$_2$ 1.07 g of the title compound was prepared in the same manner as in Catalyst Preparation Example 2, with the exception that 1.36 g (3.0 mmol) of (1S,2S)-trans-bis(diphenylphosphino)cyclohexane ligand compound was used in lieu of (S,S)-(phenyl)$_2$PCH(methyl)CH(methyl)P(phenyl)$_2$.

Catalyst Preparation Example 11

Preparation of Bis-[{(3S,4S)-trans-bis(diphenylphosphino)1-benzylpyrrolidine}chromium dichloride (μ-chloride)][CrCl$_2$(μ-Cl){(P,P)-k$^2$-(3S,4S)-(Ph$_2$P)$_2$1-benzylpyrrolidine}]$_2$ A. Preparation of Ligand (3S,4S)-trans-bis(diphenylphosphino)1-benzylpyrrolidine [(3S,4S)—(Ph$_2$P)$_2$ 1-benzylpyrrolidine 2.7 g of colorless pure (3S,4S)-trans-bis(diphenylphosphino)1-benzylpyrrolidine was prepared in the same manner as in Catalyst Preparation Example 1, with the exception that (3R,4R)-trans-1-benzylpyrrolidinediol was used as a starting material in lieu of (2R,3R)-butanediol.

B. Preparation of Bis-[{(3S,4S)-trans-bis(diphenylphosphino)1-benzylpyrrolidine}chromium dichloride (μ-chloride)][CrCl$_2$ (μ-Cl) 1 (P,P)-k$^2$-(3S,4S)—(Ph$_2$P)$_2$1-benzylpyrrolidine}]$_2$ 1.15 g of the title compound was prepared in the same manner as in Catalyst Preparation Example 2, with the exception that 1.59 g (3.0 mmol) of (3S,4S)-trans-bis(diphenylphosphino)1-benzylpyrrolidine ligand compound was used in lieu of (S,S)-(phenyl)$_2$PCH(methyl)CH(methyl)P(phenyl)$_2$.

Catalyst Preparation Example 12

Preparation of Bis-[{(S,S)-(Phenyl)$_2$PCH(methyl)CH(methyl)P(phenyl)$_2$ chromium(II) chloride (μ-chloride)][Cr(II)Cl(μ-Cl){(P,P)-k$^2$-(S,S)—((Ph)$_2$P(Me)CH—CH(Me)P(Ph)$_2$)}]$_2$ 1.51 g of the title compound was prepared in the same manner as in Catalyst Preparation Example 2, with the exception that 1.02 g (3.0 mmol) of Cr(II)Cl$_2$ was used in lieu of chromium trichloride tris-tetrahyrofuran (CrCl$_3$(THF)$_3$).

Example 1

Ethylene Oligomerization using the above-prepared Catalyst and MAO

A 600 mL stainless steel reactor was washed with nitrogen in a vacuum, and then 200 mL of cyclohexane and MAO 1.5 mmol-Al were sequentially added thereto. Then, the temperature was elevated to 45° C. In a 50 mL Schlenk flask in a glove box, 3.3 mg (0.005 mmol) of (S,S)-(phenyl)$_2$PCH(methyl)CH(methyl)P(phenyl)$_2$ chromium trichloride tetrahydrofuran of Catalyst Preparation Example 1 was mixed with 10 mL of cyclohexane, and the mixture thus obtained was added to the reactor. The reactor was charged with ethylene to 30 bar, and the mixture was stirred at 300 rpm. After 120 min, the supply of ethylene into the reactor was stopped, the stirring was stopped to terminate the reaction, and the reactor was cooled to below 10° C.

After excess ethylene in the reactor was discharged, ethanol containing 10 vol % hydrochloric acid was added to the liquid in the reactor. In order to analyze the liquid by GC-FID, nonane was added as an internal standard. A small amount of the organic layer sample was dried over anhydrous magnesium sulfate, and then analyzed by GC-FID. The remaining organic layer was filtered to separate solid wax/polymer products. These solid products were dried in an oven at 100° C. overnight and weighed, thus obtaining 1.2 g of polyethylene. GC analysis showed that the total weight of the reaction mixture was 116.2 g. The distribution of the products of this Example is summarized in Table 1 below.

Examples 2 to 12

Ethylene Oligomerization using the Above-Prepared Catalyst and MAO

Ethylene oligomerization was carried out in the same manner as in Example 1, with the exception that respective catalysts of Catalyst Preparation Examples 2 to 12 were used in appropriate amounts, and the MAO amount and the reaction time were appropriately adopted. The reaction conditions and the reaction results are shown in Table 1 below.

Comparative Example

Ethylene Tetramerization using $CrCl_3$(tetrahydrofuran)$_3$, (S,S)-(phenyl)$_2$PCH(methyl)CH(methyl)P(phenyl)$_2$ and MAO Ethylene tetramerization was carried out in the same manner as in Example 1, with the exception that 2.2 mg (0.005 mmol) of the ligand (S,S)-(phenyl)$_2$PCH(methyl)CH(methyl)P(phenyl)$_2$ [(S,S)—Ph$_2$PCH(Me)CH(Me)PPh$_2$] of Catalyst Preparation Example 1 and 1.88 mg (0.005 mmol) of $CrCl_3$(tetrahydrofuran)$_3$ were used. The reaction conditions and the reaction results are shown in Table 1 below.

TABLE 1

Ethylene Oligomerization Results

| Catalyst | Catalyst (mmol) | MAO (mmol) | Reaction Time (min) | Total Output (g) | 1-Hexene (wt %) | 1-Octene (wt %) | Polymer Solid (wt %) |
|---|---|---|---|---|---|---|---|
| Ex. 1 | 0.005 | 1.5 | 120 | 116.2 | 20.4 | 67.6 | 1.0 |
| Ex. 2 | 0.0025 | 0.7 | 90 | 253.0 | 20.0 | 69.1 | 1.0 |
| Ex. 3 | 0.0025 | 0.7 | 30 | 245.0 | 18.2 | 69.5 | 0.2 |
| Ex. 4 | 0.0025 | 0.7 | 30 | 257.5 | 17.0 | 72.3 | 0.5 |
| Ex. 5 | 0.0025 | 0.7 | 60 | 245.3 | 22.3 | 67.2 | 0.3 |
| Ex. 6 | 0.005 | 1.5 | 60 | 132.8 | 32.4 | 60.3 | 0.3 |
| Ex. 7 | 0.005 | 1.5 | 60 | 204.2 | 26.2 | 63.1 | 0.0 |
| Ex. 8 | 0.005 | 1.5 | 60 | 225.3 | 29.6 | 57.0 | 0.2 |
| Ex. 9 | 0.005 | 1.5 | 60 | 185.3 | 21.3 | 66.2 | 3.2 |
| Ex. 10 | 0.005 | 1.5 | 60 | 230.2 | 18.3 | 70.1 | 0.3 |
| Ex. 11 | 0.005 | 1.5 | 60 | 52.8 | 9.7 | 55.6 | 9.5 |
| Ex. 12 | 0.005 | 1.5 | 60 | 95.9 | 21.0 | 67.5 | 0.0 |
| C. Ex. | 0.005 | 1.5 | 60 | 16.2 | 15.6 | 68.2 | 5.3 |

With reference to the above examples and comparative example, the method of preparing the oligomer using the catalyst according to the present invention increased the output about 15 times and reduced the amount of polymer by-product from 5.3% to 0.5% or less, compared to the results of comparative example in which the ligand and the catalyst precursor were separately added.

The results of the examples showed that the structure and activity of the synthesized catalyst complex may vary depending on the synthesis solvent and conditions.

The invention claimed is:

1. A chromium complex compound for selective ethylene oligomerization comprising a chiral ligand as represented by Formula 1 or 2 below:

[Formula 1]

[Formula 2]

wherein $R^1$, $R^2$, $R^3$, and $R^4$ are each independently hydrocarbyl, substituted hydrocarbyl, heterohydrocarbyl, or substituted heterohydrocarbyl;

$R^5$ and $R^6$ are each independently hydrocarbyl or substituted hydrocarbyl, or $R^5$ and $R^6$ are bonded with hydrocarbylene, substituted hydrocarbylene, heterohydrocarbylene or substituted heterohydrocarbylene;

$X^1$ to $X^4$ are each independently halogen, —$OR^{21}$, —$OCOR^{22}$ or —$NR^{23}R^{24}$, in which $R^{21}$, $R^{22}$, $R^{23}$ or $R^{24}$ is hydrogen, hydrocarbyl or heterohydrocarbyl;

L is hydrocarbon or heterohydrocarbon; and

\* and \*\* are a chiral carbon position and are each independently (S) or (R) configuration.

2. The chromium complex compound of claim 1, comprising a chiral ligand represented by Formulas 3 to 8 below:

[Formula 3]

(R),(R)-Chiraphos-mono Chromium complex

[Formula 4]

(S),(S)-Chiraphos-mono Chromium complex meso-Chiraphos-mono Chromium complex (R),(R)-Chiraphos-bis Chromium complex (S),(S)-Chiraphos-bis Chromium complex meso-Chiraphos-bi Chromium complex wherein substituents $R^1$ to $R^6$ and $X^1$ to $X^4$ of Formulas 2 to 6 are defined as in claim 1;

wherein $R^7$, $R^8$, $R^9$ and $R^{10}$ are each independently hydrocarbyl, substituted hydrocarbyl, heterohydrocarbyl, or substituted heterohydrocarbyl;

$R^{11}$ and $R^{12}$ are each independently hydrocarbyl or substituted hydrocarbyl, or $R^{11}$ and $R^{12}$ are bonded with hydrocarbylene, substituted hydrocarbylene, heterohydrocarbylene or substituted heterohydrocarbylene; and

$X^5$ and $X^6$ are each independently halogen, —$OR^{21}$, —$OCOR^{22}$ or —$NR^{23}R^{24}$, in which $R^{21}$, $R^{22}$, $R^{23}$ or $R^{24}$ is hydrogen, hydrocarbyl or heterohydrocarbyl.

3. The chromium complex compound of claim 1, wherein substituents $R^1$, $R^2$, $R^3$, $R^4$, $R^7$, $R^8$, $R^9$ and $R^{10}$ of the chiral ligand are each independently (C6-C20)aryl, (C6-C20)ar(C1-C10)alkyl, (C1-C10)alkyl, (C2-C10)alkenyl, (C2-C10)alkynyl, (C3-C7)cycloalkyl, hetero(C5-C20)aryl, hetero(C3-C7)cycloalkyl, or —$NR^{23}R^{24}$ in which $R^{23}$ or $R^{24}$ is (C1-C10)alkyl or (C6-C20)aryl, and the substituents $R^1$, $R^2$, $R^3$, $R^4$, $R^7$, $R^8$, $R^9$ and $R^{10}$ may be further substituted by one or more selected from among (C1-C10)alkyl, (C1-C10)alkoxy, (C6-C20)aryloxy and halogen, $R^5$, $R^6$, $R^{11}$ and $R^{12}$ are each independently (C6-C20)aryl, (C6-C20)ar(C1-C10)alkyl, (C1-C10)alkyl, (C2-C10)alkenyl, (C2-C10)alkynyl, (C3-C7)cycloalkyl, hetero(C5-C20)aryl, hetero(C3-C7)cycloalkyl, (C1-C10)alkoxy, (C6-C20)aryloxy, aminocarbonyl, carbonylamino, di(C1-C10)alkylamino, (C1-C10)alkylsilyl or (C6-C20)arylsilyl, and the substituents $R^5$, $R^6$, $R^{11}$ and $R^{12}$ may be substituted by (C1-C10)alkyl, (C1-C10)alkoxy, (C6-C20)aryloxy and halogen.

4. The chromium complex compound of claim 3, wherein the $R^1$, $R^2$, $R^3$, $R^4$, $R^7$, $R^8$, $R^9$ and $R^{10}$ of the chiral ligand are each independently selected from the group consisting of phenyl, naphthyl, anthracenyl, mesityl, xylyl, methyl, ethyl, ethylenyl, n-propyl, i-propyl, propenyl, propynyl, n-butyl, t-butyl, cyclopropyl, cyclobutyl, cyclopentyl, cyclohexyl, 4-methylcyclohexyl, 4-ethylcyclohexyl, 4-isopropylcyclohexyl, benzyl, tolyl, xylyl, 4-methylphenyl, 4-ethylphenyl, 4-isopropylphenyl, 4-t-butylphenyl, 4-methoxyphenyl, 4-isopropoxyphenyl, cumyl, methoxy, ethoxy, phenoxy, tolyloxy, dimethylamino, thiomethyl, trimethylsilyl, dimethylhydrazyl, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl, o-isopropoxyphenyl, biphenyl, naphthyl and anthracenyl, and $R^5$, $R^6$, $R^{11}$ and $R^{12}$ are each independently selected from the group consisting of methyl, ethyl, ethylenyl, n-propyl, i-propyl, propenyl, propynyl, n-butyl, t-butyl, i-butyl, phenyl, benzyl, tolyl, xylyl, methoxy, ethoxy, phenoxy, methylamino, and dimethylamino.

5. The chromium complex compound of claim 4, wherein the $R^1$, $R^2$, $R^3$, $R^4$, $R^7$, $R^8$, $R^9$ and $R^{10}$ of the chiral ligand are each independently selected from the group consisting of phenyl, benzyl, naphthyl, 4-methylphenyl, 4-ethylphenyl, 4-isopropylphenyl, 4-t-butylphenyl, 4-methoxyphenyl, 4-isopropoxyphenyl, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl and o-isopropoxyphenyl.

6. The chromium complex compound of claim 1, comprising a chiral ligand represented by one of Formulae 9 to 14 below:

1,2-(R),(R)-trans-Cyclophos-mono Chromium complex 1,2-(S),(S)-trans-Cyclophos-mono Chromium complex -continued

[Formula 11]

1,2-(R),(S)-cis-Cyclophos-mono Chromium complex

[Formula 12]

1,2-(R),(R)-trans-Cyclophos-bi Chromium complex

[Formula 13]

1,2-(S),(S)-trans-Cyclophos-bi Chromium complex

[Formula 14]

1,2-meso-cis-Cyclophos-bi Chromium complex wherein A of the chiral ligand is selected from among (C1-C5)alkylene and (C1-C5)alkenylene.

7. The chromium complex compound of claim 1, wherein the chiral ligand of Formula 1 or 2 is selected from among (S,S)-, (R,R)- or meso-(phenyl)$_2$P—CH(methyl)CH(methyl)-P(phenyl)$_2$, (S,S)-, (R,R)- or meso-(4-methoxyphenyl)$_2$P—CH(methyl)CH(methyl)-P(4-methoxyphenyl)$_2$, (S,S)-, (R,R)- or meso-(4-methylphenyl)$_2$P—CH(methyl)CH(methyl)-P(4-methylphenyl)$_2$, (S,S)-, (R,R)- or meso-(4-ethylphenyl)$_2$P—CH(methyl)CH(methyl)-P(phenyl)$_2$, (S,S)-, (R,R)- or meso-(4-ethylphenyl)$_2$P—CH(ethyl)CH(methyl)-P(4-ethylphenyl)$_2$, (S,S)-, (R,R)- or meso-(4-methoxyphenyl)$_2$P—CH(ethyl)CH(methyl)-P(phenyl)$_2$, (S,S)-, (R,R)- or meso-(4-ethylphenyl)$_2$P—CH(ethyl)CH(ethyl)-P(4-ethylphenyl)$_2$, (S,S)-, (R,R)- or meso-(phenyl)$_2$P—CH(ethyl)CH(ethyl)-P(phenyl)$_2$, (R,R)— or meso-(phenyl)$_2$P—CH(isopropyl)CH(methyl)-P(phenyl)$_2$, (S,S)-, (R,R)- or meso-(4-methoxyphenyl)$_2$P—CH(isopropyl)CH(methyl)-P(4-methoxyphenyl)$_2$, (S,S)-, (R,R)- or meso-(4-ethylphenyl)$_2$P—CH(isopropyl)CH(methyl)-P(4-ethylphenyl)$_2$, (S,S)-, (R,R)- or meso-(phenyl)$_2$P—CH(n-propyl)CH(methyl)-P(phenyl)$_2$, (S,S)-, (R,R)- or meso-(4-methoxyphenyl)$_2$P—CH(n-propyl)CH(methyl)-P(4-methoxyphenyl)$_2$, (S,S)-, (R,R)- or meso-4(4-ethylphenyl)$_2$P—CH(n-propyl)CH(methyl)-P(4-ethylphenyl)$_2$, (S,S)-, (R,R)- or meso-(phenyl)$_2$P—CH(isopropyl)CH(ethyl)-P(phenyl)$_2$, (S,S)-, (R,R)- or meso-(4-methoxyphenyl)$_2$P—CH(isopropyl)CH(ethyl)-P(4-methoxyphenyl)$_2$, (S,S)-, (R,R)- or meso-(4-ethylphenyl)$_2$P—CH(isopropyl)CH(ethyl)-P(4-ethylphenyl)$_2$, (S,S)-trans, (R,R)-trans- or meso-cis-1,2-di-(P(phenyl)$_2$)cyclohexane, (S,S)-trans, (R,R)-trans- or meso-cis-1,2-di-(P(4-methoxyphenyl)$_2$)cyclohexane, (S,S)-trans, (R,R)-trans- or meso-cis-1,2-di-(P(4-ethylphenyl)$_2$)cyclohexane, (S,S)-trans, (R,R)-trans- or meso-cis-trans-1,2-di-(P(phenyl)$_2$)cyclopentane, (S,S)-trans, (R,R)-trans- or meso-cis-1,2-di-(P(4-methoxyphenyl)$_2$)cyclopentane, (S,S)-trans, (R,R)-trans- or meso-cis-1,2-di-(P(4-ethylphenyl)$_2$)cyclopentane, (S,S)-trans, (R,R)-trans- or meso-cis-3,4-di-(P(phenyl)$_2$)pyrrole, (S,S)-trans, (R,R)-trans- or meso-cis-3,4-di-(P(4-methoxyphenyl)$_2$)pyrrole, (S,S)-trans, (R,R)-trans- or meso-cis-3,4-di-(P(4-ethylphenyl)$_2$)pyrrole, (S,S)-trans, (R,R)-trans- or meso-cis-3,4-di-(P(4-ethylphenyl)$_2$)imidazole, (S,S)-, (R,R)- or meso-(4-ethylphenyl)$_2$P—CH(dimethylamine)CH(dimethylamine)-P(4-ethylphenyl)$_2$, (S,S)-, (R,R)- or meso-(3-methoxyphenyl)$_2$P—CH(methyl)CH(methyl)-P(3-methoxyphenyl)$_2$, (S,S)-, (R,R)- or meso-(4-ethoxyphenyl)$_2$P—CH(methyl)CH(methyl)-P(o-ethoxyphenyl)$_2$, (S,S)-, (R,R)- or meso-4-(dimethylaminephenyl)$_2$P—CH(methyl)CH(methyl)P(4-dimethylaminephenyl)$_2$, (S,S)-, (R,R)- or meso-(4-ethylcyclohexyl)$_2$PCH(methyl)CH(methyl)P(4-ethylcyclohexyl)$_2$, (S,S)-, (R,R)- or meso-(2-ethylphenyl)$_2$PCH(methyl)CH(methyl)P(2-ethylphenyl)$_2$, (S,S)-, (R,R)- or meso-(2-isopropylphenyl)$_2$PCH(methyl)CH(methyl)P(2-isopropylphenyl)$_2$, (S,S)-, (R,R)- or meso-(2-methylphenyl)$_2$PCH(methyl)CH(methyl)P(2-methylphenyl)$_2$, (S,S)-, (R,R)- or meso-(2-ethylphenyl)$_2$PCH(methyl)CH(methyl)P(phenyl)$_2$, (S,S)-, (R,R)- or meso-(2-ethylphenyl)$_2$PCH(ethyl)CH(methyl)P(2-ethylphenyl)$_2$, (S,S)-, (R,R)- or meso-(2-ethylphenyl)$_2$PCH(ethyl)CH(ethyl)P(2-ethylphenyl)$_2$, (S,S)-, (R,R)- or meso-(2-ethylphenyl)$_2$PCH(isopropyl)CH(methyl)P(2-ethylphenyl)$_2$, (S,S)-, (R,R)- or meso-(2-ethylphenyl)$_2$PCH(n-propyl)CH(methyl)P(2-ethylphenyl)$_2$, (S,S)-, (R,R)- or meso-(2-ethylphenyl)$_2$PCH(isopropyl)CH(ethyl)P(2-ethylphenyl)$_2$, (S,S)-trans, (R,R)-trans- or meso-cis-1,2-di-(P(2-ethylphenyl)$_2$)cyclohexane, (S,S)-trans, (R,R)-trans- or meso-cis-1,2-di-(P(2-ethylphenyl)$_2$)cyclopentane, (S,S)-trans, (R,R)-trans- or meso-cis-3,4-di-(P(2-ethylphenyl)$_2$)pyrrole, (S,S)-trans, (R,R)-trans- or meso-cis-3,4-di-(P(2-ethylphenyl)$_2$)imidazole, (S,S)-, (R,R)- or meso-(2-ethylphenyl)$_2$PCH(dimethylamine)CH(dimethylamine)P(2-ethylphenyl)$_2$, (S,S)-, (R,R)- or meso-(2-methoxyphenyl)$_2$PCH(methyl)CH(methyl)P(2-methoxyphenyl)$_2$, (S,S)-, (R,R)- or meso-(2-ethoxyphenyl)$_2$PCH(methyl)CH(methyl)P(2-ethoxyphenyl)$_2$, (S,S)-, (R,R)- or meso-(2-dimethylaminephenyl)$_2$PCH(methyl)CH(methyDP(2-dimethylaminephenyl)$_2$, and (S,S)-, (R,R)- or meso-(2-ethylcyclohexyl)$_2$PCH(methyl)CH(methyl)P(2-ethylcyclohexyl)$_2$.

8. The chromium complex compound of claim 1, wherein the $X^1$, $X^2$, $X^3$, $X^4$, $X^5$ or $X^6$ is selected from among Cl, Br, acetoacetyl and 2-ethylhexanoyl.

9. The chromium complex compound of claim 1, wherein the L is selected from among tetrahydrofuran, diethylether, toluene, chlorobenzene, dichlorobenzene, acetylacetone and 2-ethylhexanone.

10. A chromium complex catalyst composition for selective ethylene oligomerization, comprising the chromium complex compound of claim 1 and a co-catalyst.

11. The chromium complex catalyst composition of claim 10, wherein the co-catalyst is an organoaluminum compound, an organoboron compound, an organic salt, phosphorus or mixtures thereof.

12. The chromium complex catalyst composition of claim 11, wherein the co-catalyst is methylaluminoxane (MAO), modified methylaluminoxane (MMAO), ethylaluminoxane (EAO), trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, or methylaluminum sesquichloride.

13. The chromium complex catalyst composition of claim 11, wherein the chromium complex and the aluminoxane are mixed such that a molar ratio of aluminum to chromium is 1:1~10, 000:1.

14. A method of selectively preparing 1-hexene from ethylene using the chromium complex compound of claim 1.

15. A method of selectively preparing 1-octene from ethylene using the chromium complex compound of claim 1.

16. The method of claim 14, wherein a reaction solvent is diethylether, toluene, chlorobenzene, dichlorobenzene, acetylacetone, or mixtures thereof.

17. The method of claim 15, wherein a reaction solvent is diethylether, toluene, chlorobenzene, dichlorobenzene, acetylacetone, or mixtures thereof.

* * * * *